US009193671B2

(12) United States Patent
Durham et al.

(10) Patent No.: US 9,193,671 B2

(45) Date of Patent: Nov. 24, 2015

(54) ANTI-AGGLOMERATE GAS HYDRATE INHIBITORS FOR USE IN PETROLEUM AND NATURAL GAS SYSTEMS

(75) Inventors: Danny Durham, Houston, TX (US); Curtis Conkle, Houston, TX (US); James Russum, Houston, TX (US)

(73) Assignee: Multi-Chem Group, LLC, San Angelo, TX (US)

( * ) Notice: Subject to any disclaimer, the term of this patent is extended or adjusted under 35 U.S.C. 154(b) by 1094 days.

(21) Appl. No.: 13/245,580

(22) Filed: Sep. 26, 2011

(65) Prior Publication Data

US 2012/0078021 A1 Mar. 29, 2012

Related U.S. Application Data

(63) Continuation-in-part of application No. 13/238,757, filed on Sep. 21, 2011.

(60) Provisional application No. 61/385,033, filed on Sep. 21, 2010.

(51) Int. Cl.

| | |
|---|---|
| ***C07C 7/20*** | (2006.01) |
| ***C07C 211/63*** | (2006.01) |
| ***C07C 57/145*** | (2006.01) |
| ***C07C 63/06*** | (2006.01) |
| ***C07C 63/26*** | (2006.01) |
| ***C07C 65/10*** | (2006.01) |

(Continued)

(52) U.S. Cl.

CPC ................. *C07C 211/63* (2013.01); *C07C 7/20* (2013.01); *C07C 57/145* (2013.01); *C07C 63/06* (2013.01); *C07C 63/26* (2013.01); *C07C 65/10* (2013.01); *C07C 309/04* (2013.01); *C09K 8/52* (2013.01); *C09K 2208/22* (2013.01)

(58) Field of Classification Search

None

See application file for complete search history.

(56) References Cited

U.S. PATENT DOCUMENTS

| | | | | |
|---|---|---|---|---|
| 6,444,852 | B1 | 9/2002 | Milburn et al. | |
| 6,566,309 | B1 * | 5/2003 | Klug et al. | 507/90 |
| 8,183,185 | B2 * | 5/2012 | Pakulski | 507/241 |

(Continued)

FOREIGN PATENT DOCUMENTS

| | | | |
|---|---|---|---|
| WO | 03/006583 | A1 | 1/2003 |
| WO | 2005/042675 | A2 | 5/2005 |

(Continued)

OTHER PUBLICATIONS

D.D. Perrin, W.L.F. Armarego, D.R. Perrin, Purification of laboratory chemicals, Pergaman Press, 1980 (2nd Ed.), pp. 20-25.

*Primary Examiner* — John J Figueroa

(74) *Attorney, Agent, or Firm* — Holly Soehnge; Baker Botts L.L.P.

(57) ABSTRACT

A method of inhibiting gas hydrate formation in petroleum and natural gas production systems through the use of low dosage hydrate inhibitors which include reaction products of non-halide-containing inorganic acids, organic acids, and organic amines. The use of these non-halide-containing reaction products rather than chloride containing acids or alkylating agents avoids corrosion and stress cracking caused by residual inorganic chloride and other inorganic, halide-containing acids. The anti-agglomerate compositions can be administered continuously to effectively inhibit gas hydrate formation. In preferred embodiments, the anti-agglomerate compositions are mixtures of reaction products of non-halide-containing organic acids and organic amines.

4 Claims, 4 Drawing Sheets

(51) Int. Cl.
*C07C 309/04* (2006.01)
*C09K 8/52* (2006.01)

(56) References Cited

U.S. PATENT DOCUMENTS

2005/0261529 A1* 11/2005 Crosby et al. .................. 585/15
2006/0120051 A1 6/2006 Macris et al.
2006/0135372 A1 6/2006 Hossaini et al.
2008/0041228 A1 2/2008 Seibert
2008/0064611 A1* 3/2008 Spratt ............................ 507/90
2009/0173663 A1 7/2009 Leinweber et al.

FOREIGN PATENT DOCUMENTS

WO 2005/042675 A3 9/2005
WO 2009/042319 A1 4/2009

* cited by examiner (a)

(b)

ANTI-AGGLOMERATE GAS HYDRATE INHIBITORS FOR USE IN PETROLEUM AND NATURAL GAS SYSTEMS

BACKGROUND

The systems and methods described herein pertain to the production of petroleum products and natural gas, and particularly to compositions effective as anti-agglomerate low dosage gas hydrate inhibitors ("LDHI's") for the prevention of gas hydrate plugs.

Gas hydrates are solids that may form during hydrocarbon production, in particular in pipelines and other equipment, that may impede or completely block flow of hydrocarbons. These blockages not only decrease or stop production, potentially costing millions of dollars in lost production, but are also very difficult and dangerous to mediate. Unless properly handled, gas hydrates may explode, rupturing pipelines, damaging equipment, endangering workers and putting at risk the ocean environment.

Gas hydrates may form when water molecules become bonded together after coming into contact with certain "guest" gas molecules. Hydrogen bonding causes the water molecules to form a regular lattice structure that is stabilized by the guest gas molecules. The resulting crystalline structure precipitates as a solid gas hydrate. Guest molecules can include any number of molecules, including carbon dioxide, methane, butane, propane, hydrogen, helium, freons, halogens, and noble gases.

Thermodynamic, anti-agglomerate, and kinetic inhibitors are three general classes of hydrate inhibitors. Thermodynamic inhibitors are most commonly used. Thermodynamic inhibitors, such as methanol and ethylene glycol must typically be used at high concentrations to be effective, concentrations that may present environmental concerns. For instance, methanol is used in concentrations of up to 50% methanol to water ratio, with glycol as much as 30% glycol to water. Methanol presents other challenges, as it is flammable and can be corrosive. Thus, thermodynamic inhibitors are often not appropriate for many drilling operations, particularly environmentally-sensitive drilling operations.

Kinetic inhibitors and anti-agglomerate inhibitors typically function at lower concentrations than thermodynamic inhibitors and are therefore termed LDHI's. Kinetic hydrate inhibitors are polymers that may prevent or delay the nucleation of hydrates. Thus the kinetic hydrate inhibitors limit hydrate crystal size and growth such that hydrate plugs are not allowed to form in tubular goods. However, kinetic hydrate inhibitors are capable of handling only low-to moderate subcooling—typically subcooling of about 10-25° F. (subcooling is the difference between the operating temperature of the hydrocarbon system and the temperature at which hydrates would form at the same operating pressure). Thus, kinetic hydrate inhibitors may not be suitable in deep and ultra-deep wells, where subcooling may be greater than 30° F.

Anti-agglomerate gas inhibitors are typically more cost effective than thermodynamic inhibitors, as they may be used in much lower concentrations and are typically useful in environments with greater subcooling than would be appropriate for kinetic inhibitors. However, many of the traditional anti-agglomerate LDHI's contain residual halides, such as HCl, HBr, and the like, and residual organic halides. Residual halides have been know to cause corrosion and stress corrosion cracking ("SCC") in metal piping and production equipment. One example of a commonly used anti-agglomerate LDHI is quaternary anti-agglomerates containing residual organic halides, such as Kelland, 2006. As an example, Milburn et al. U.S. Pat. No. 6,444,852 entitled "Amines Useful in Inhibiting Gas Hydrate Formation," which is hereby incorporated by reference in its entirety, describes anti-agglomerate ether-containing amine compounds that are quaternized with a halide. Especially in the case of organic halides, they can be very toxic and environmentally unfriendly. This is particularly true when the inhibitors are applied continuously. In addition, traditional anti-agglomerate LDHI's may break down and become less effective when exposed to high temperatures above 250° F.

What is needed is an anti-agglomerate LDHI that does not contain residual halides in sufficient quantities to present an inappropriate risk of corrosion or stress cracking and that is less toxic and more environmentally friendly than the traditional LDHI's.

SUMMARY

The present disclosure relates generally to the field of gas and oil production. Other uses may also be made of same. In particular, compositions and methods for inhibiting the formation of gas hydrate plugs are described.

Compositions are described which are anti-agglomerate low dosage hydrate inhibitors ("AA-LDHI"s) that are made without the use of organic chlorides or halides to minimize residual organic halides other resultant inorganic halides that are respectively highly toxic and corrosive. Examples of such halides include HF, HCl, HBr, HI, and the like. These new AA-LDHI's can be injected continuously without concern for high corrosion rates or stress corrosion cracking of injection equipment and production metal goods caused by residual halides such as HCl, HBr, and the like. While the compositions are structurally similar to quaternary amines, they are reaction products of organic acids and organic amines that eliminate or substantially reduce residual inorganic or organic halides (MX), and/or residual hydrogen halides (HCl, HBr, HI, and the like). Inorganic halides (MX), and/or residual HX are often created as byproducts when quaternary salts are produced using chlorinated or halogenated alkylating agents. These agents typically include benzyl chloride, bromide, iodide, or the like, of the structure R—X wherein R is any organic structure. This byproduct formation is due to their reaction with water either during or after the reaction. In the current compositions, instead of a halide anion being associated with the quaternary ammonium cation, an organic acid anion is present. This is a significant difference that distinguishes the described compositions from other anti-agglomerate compounds. In some preferred embodiments, the anti-agglomerate low dosage hydrate inhibitors are mixtures of organic reaction products of organic acids and organic amines, including but not limited to those including fatty acids and fatty amines.

The described compositions effectively inhibit the formation of gas hydrates in petroleum and natural gas production systems without the negative effects associated with residual chlorides or other halides, such as high corrosion rates, stress cracking, and potential high toxicity.

DETAILED DESCRIPTION OF PREFERRED EMBODIMENTS

The current anti-agglomerate compositions include mixtures of reaction products of non-halide-containing inorganic acids and/or organic acids with organic amines. The reaction products are structurally similar to other quaternary amine halide analogs, but the reaction products lack acid halides, inorganic halides, and organic halides. Certain embodiments include mixtures of reaction products of organic acids and organic amines, including an anti-agglomerate low dosage hydrate inhibitor that is free of acid halides, inorganic halides, and organic halides and that can be injected continuously with minimized concern for corrosion, stress corrosion cracking, or highly toxic reactants or reaction products.

Figure 1:
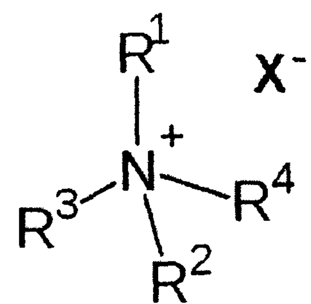
FIG. 1 shows a general structure of a quaternary ammonium salt having a chloride or other halide anion, wherein $R^1$, $R^2$, $R^3$, and $R^4$ are generally and independently H or $C_1$-$C_{40}$, and X is generally F, Cl, Br, I, other halides, or similar suitable substituents.

FIG. 1 shows a traditional example of a quaternary ammonium salt utilizing a halide as an anion. The quaternary ammonium cation is that portion of the molecule that has a positive charge, $NR_1R_2R_3R_4^+$. The term quaternary amine is often used to refer to the positively charged quaternary ammonium compound. In a quaternary ammonium cation, $R_1$, $R_2$, $R_3$, and $R_4$ can be any number of suitable constituents, including hydrogen (H), methyl ($CH_3$), ethyl ($CH_2CH_3$), acetyl ($COCH_3$), other alkyl or aryl groups of varying lengths and structures, and others. Some of the R constituents may also be connected to each other. Those of skill in the art with the benefit of this disclosure will understand the varying natures of the R constituents.

In the reaction or manufacturing processes to form quaternary ammonium halides for use as AA-LDHIs, it is common to form hydrogen halides and organic alcohols due to residual water present during and left over in the reaction mixtures. This is due to the reaction of R—X with HOH($H_2O$) to form ROH and HX. This is generally due to having to use an excess of RX to drive the reaction. In some cases as much as 1% of the RX (e.g. benzyl chloride and the like) is found in the final reaction mixture that eventually converts to HX (HCl and the like) and ROH and mixtures thereof. In some cases it has been found that acid corrosion inhibitors are required to mitigate the acid corrosion caused by the residual HCl. In addition, the residual RX can prove to have some severe acute and chronic toxicity.

Figure 2:
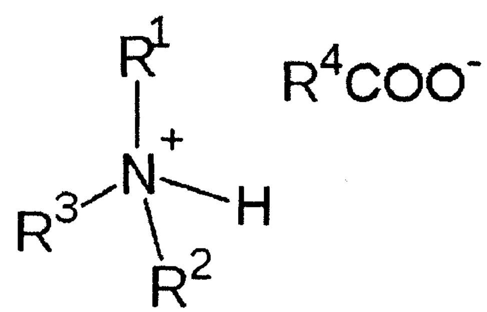
FIG. 2 shows general structures (a) and (b) of organic reaction products of organic acids and organic amines having an organic anion, wherein $R^1$, $R^2$, and $R^3$ are independently H or $C_1$-$C_{40}$, including all alkyl and aryl structures and isomers, and wherein $R^4$ is $C_1$-$C_{40}$, including all alkyl and aryl structures and isomers.
Figure 2:
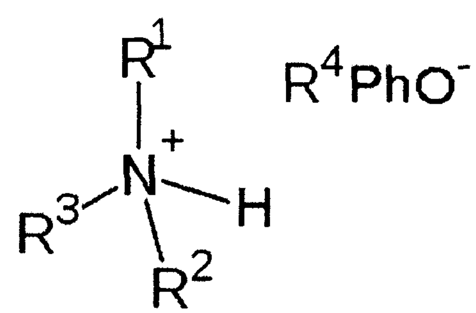

In one embodiment of the present disclosure, the anti-agglomerate LDHI is the reaction products of organic acid and organic amines. Reaction products of organic acids and organic amines are formed when certain organic acids are partially neutralized, giving them at least a partial negative charge that enables them to serve as anions in a salt. FIG. 2 shows some general examples of reaction products or organic acids and organic amines having the structure $R^1R^2R^3HN^+(R^4COO^-)$ or $R^1R^2R^3HN^+(R^4PhO^-)$ wherein $R^1$, $R^2$, and $R^3$ are independently H or $C_1$-$C_{40}$, wherein $R^4$ is $C_1$-$C_{40}$, and wherein Ph is any phenyl group. The substituents $C_1$-$C_{40}$ include all alkyl and aryl structures and isomers within these embodiments. In these examples, the negatively charged anions are anions created by partial or complete neutralization of acids. Certain embodiments can include reactions or mixtures that include varying ratios of the organic acid, organic amine, and the resulting salt of the reaction of the organic acid and amine. In certain embodiments of the present disclosure, approximately stoichiometric amounts of the organic acid and amine are used to create the resultant salt. In other embodiments of the present invention, molar ratios of the reactants are adjusted so as to create a surplus of free organic amine in the resultant reaction product. Typically, the excess amine is less than about 1% (by mol) of the reaction product.

The compounds that can be used as cations with the desired acid anions can be any suitable non-halide-containing amines. As discussed with regard to FIG. 1, $R_1$, $R_2$, and $R_3$, can be any suitable substituents, including hydrogen (H), methyl ($CH_3$), ethyl ($CH_2CH_3$), acetyl ($COCH_3$), and other alkyl or aryl groups of varying lengths. Some of the R substituents may also be connected to each other and can include oxygen, nitrogen, and the like. Those of skill in the art with the benefit of this disclosure will understand the varying natures of the R substituents within the cation. Examples of suitable cations include, but are not limited to ammonia, methylamine, di methylamine, trimethylamine, ethylamine, di ethylamine, tri ethylamine, n-propylamine, di-n-proplyamine, tri-n-propylamine, monoethanolamine, di ethanolamine, diethyl ethanaol amine, methyl ethanol amine, tri ethanol amine, methyl diethanol amine, propyl ethanolamine, ethyl diethanol amine, di methyl amino propyl amine, di propyl ethanol amine, di-n-butyl amine, di butyl propanol amine, dibutyl ethanolamine, morpholine, piperazine, octyl amine, dimethyl octyl amine, decyl amine, di methyl decyl amine, lauryl amine, dimethyl laurylamine, myristyl amine, dimethyl palmityl amine, stearyl amine, di methyl stearyl amine, di-stearyl amine, N,N dibutyl coco amido propylamine, N,N dimethyl coco amido propylamine cocoamine, cocodiamine, dimethyl cocoamine, tallowamine, tallow diamine, di methyl tallow amine, soya amine, dimethyl soya amine, di dodecyl mono methylamine, fatty imidazolines, fatty amido-amines, fatty amines, and mixtures thereof.

The compounds that can be used as anions with the cations discussed above can also be any suitable non-halide-containing acids. As discussed with regard to FIG. 1, $R_4$ can be any suitable constituents, including hydrogen (H), methyl ($CH_3$), ethyl ($CH_2CH_3$), acetyl ($COCH_3$), and other alkyl or aryl groups of varying lengths, and can include oxygen, nitrogen, and the like. Examples of suitable anions include formic acid, acetic acid, lactic acid, cyanuric acid, angelic acid, propionic acid, butyric acid, aspartic acid, glycolic acid, adipic acid, maleic acid, citric acid, phthalic acid, anthranilic acid, octanoic acid, lauric acid, benzoic acid, salicylic acid, fumaric acid, oxalic acid, succinic acid, acrylic acid, cinnamic acid, azelaic acid, neodecanoic acid, benzilic acid, pelargonic acid, stearic acid, dimer acid, trimer acid, varying ratios of dimer-trimer acid blends, methane sulfonic acid, dodecyl benzene sulfonic acid, para-toluenene sulfonic acid, oleic acid, tall oil fatty acid, linoleic acid, abietic acid, rosin acid, napthenic acid, carboxylic acids and anhydrides thereof, phenols, sulfonic acids, sulfuric acid, phosphoric acid, nitric acid or mixtures thereof. Those of skill in the art with the benefit of this disclosure will understand the varying natures of the R constituent within the anion.

As those of skill in the art with the benefit of the present disclosure will appreciate, certain salts made in accordance with the present disclosure will have superior performance characteristics to other salts. As described in U.S. Pat. No. 5,460,728 to Klomp et al., which is incorporated herein by reference, compounds suitable for use as AA-LDHI's will have at least some of the following characteristics:

Inhibit hydrate crystal growth;

Emulsify into the hydrocarbon phase, thereby keeping the concentration of water available for hydrate forming at the conduit wall small;

Concentrate near the water-hydrocarbon interfaces, where hydrate formation is most pronounced, thereby raising the local concentration of ions to freezing-point depressing level;

Modify the structure of water near the hydrocarbon-water interface in such a way that the formation of hydrate crystals is hindered;

Impeded further access of water molecules to the hydrate crystal after attachment of the subject compound to the hydrate crystals;

Prevent agglomeration of hydrate crystals by making their surface hydrophobic;

Adhere to the conduit wall, thereby preventing the adhesion of hydrates thereto.

Examples of salts that meet one or more criteria above include the reaction product of a 1:1 molar ratio of benzoic acid and dimethyl palmitoyl amine, a 2:1 molar ratio of phthalic anhydride and cocodiamine, and a 2:1 molar ratio of salicylic acid and cocodiamine.

Figure 3:
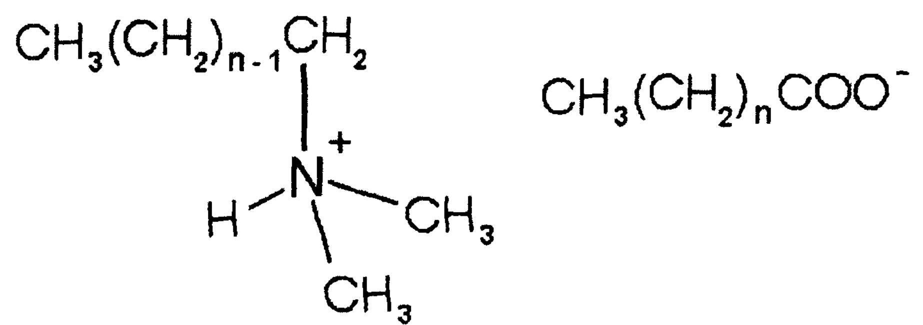
FIG. 3 shows a preferred embodiment of a general structure of the reaction product of a coconut oil based amine and a fatty coconut oil based acid, wherein n is 8-12.

Certain reaction products of organic acids and organic amines derived from coconut oil have the structure $[CH_3(CH_2)_n(CH_3)_2HN+][CH_3(CH_2)_nCOO-]$. FIG. 3 shows a general representation of these possible reaction products of a coconut oil based amine and acid in which n can be varied from, for example, 8 to 12. This is an exemplary embodiment that in no way limits the scope of the anti-agglomerate compositions overall.

Reaction products of organic acids and organic amines are more advantageous than traditional AA-LDHIs made from alkyl or aryl halides in several respects. In the reaction or manufacturing processes to form quaternary ammonium halides for use as AA-LDHIs it is common to form hydrogen halides and organic alcohols due to residual water present during and left over in the reaction mixtures. The reactants and reaction products in the current AA-LDHI compositions are not as corrosive as the likes of HCl or HX, do not cause halide stress cracking, and are not as toxic. Because of these advantages, the anti-agglomerate compositions can be injected continuously into petroleum and natural gas systems. Methods of continuous injection include via umbilical or cap string. Batch applications are also suitable. The anti-agglomerate compositions can be applied at a concentration of about 0.05% to about 10%, and preferably at about 0.2% to about 1.5%.

Without wanting to be bound by theory, anti-agglomerate compositions comprised of mixtures of reaction products of organic acids and organic amines work by helping to emulsify water in oil. It is generally agreed that anti-agglomerate LDHI molecules need hydrocarbon to function and tend to emulsify water as an internal emulsion phase. This limits the growth and size of hydrate crystals to a form and size that does not allow the hydrates formed to plug production equipment.

The current anti-agglomerate compositions have distinct advantages over those anti-agglomerate compositions already commercially available, as all of these compositions contain residual chlorides. One advantage is the difference in corrosivity, which stems from the basic differences in corrosivity between inorganic acids such as HX or HCl and that of organic acids. The pKa associated with FIX is much less than that associated with COOH. The current AA-LDHIs potentially resolve long term corrosion issues present with chlorides or HCl that are formed or are inherent in the quat type products typically used where continuous anti-agglomerate injection is required. Chloride stress corrosion cracking or hydrogen penetration is accelerated by the trace HCl formed in the reaction of R—Cl/R—X in quat manufacturing that has proven to be an issue in continuous versus batch use of quat based AA-LDHI. Testing has shown that the current anti-agglomerate compositions are equal to if not superior to the industry standard in performance. In addition, the current, non-quat anti-agglomerate compositions have greater oil solubility for reduction of water quality issues. This leads to increased "greenness" or environmental compatibility by partitioning more to the oil phase. The current compositions also lack certain inherent chronic or carcinogenic toxicity characteristics associated with residual RCl, Rx, and other organic chloride or halide found in traditional AA-LDHIs, including vinyl chloride, benzyl chloride, alkyl bromides, and the like.

Further, AA-LDHIs made in accordance with the present disclosure have better stability at higher temperatures than traditional AA-LDHIs. In certain applications, it may be necessary for the AA-LDHI to be subjected to temperatures in excess of 250° F. Certain traditional AA-LDHIs, such as those made from quatenary amines, are known to degrade at higher temperatures, resulting in a reduction of efficiency in controlling hydrates. Those AA-LDHIs made in accordance with the present disclosure retain efficacy after exposure to temperatures in excess of 250° F.

In addition, unlike traditional AA-LDHIs, AA-LDHs made in accordance with the present disclosure, function as corrosion inhibitors. Corrosion in the production from oil and gas often is often as a result of the presence of water in the production equipment, either produced from the formation, from condensation, or from water injected into the well, for instance, for lift assist. Hydrogen sulfide ($H_2S$) and carbon dioxide ($CO_2$) are often present in produced fluids, which can, in the presence of water, form acids such as sulfuric and carbonic acids (respectively). Oxygen, when present, may also contribute to corrosivity and is sometimes a contaminant in the water used for injection.

The AA-LDHIs of the present disclosure may, in addition to serving as AA-LDHIs, may function as corrosion inhibitors by contacting and coating the exposed metal of the oil and gas production equipment and piping. The exposed metal, after being coated, by the corrosion inhibitor, prevents subsequent corrosion of the surface by the corrosive agents in the hydrocarbon stream.

Corrosion inhibitors are normally delivered to through an umbilical to the oil and gas production equipment and piping. The additional use of the AA-LDHIs of the present disclosure as corrosion inhibitors has the benefit of both reducing costs to the driller by eliminating an additional on-site chemical, but also by eliminating the umbilical used to deliver the traditional corrosion inhibitor.

EXAMPLE 1

Four AA-LDHIs made in accordance with the present disclosure were tested and compared to determine their effectiveness to prevent formation of hydrate crystals in gas production systems. The four AA-LDHIs tested were benzoic acid/dimethyl palmitoyl amine mixed in a 1:1 molar ratio, maleic anhydride/dimethyl palmitoyl amine mixed in a 1:1 molar ratio, methanesulfonic acid/cocodiamine mixed in a 2:1 molar ratio, phthalic anhydride/cocodiamine mixed in a 2:1 molar ratio, and salicylic acid/cocodiamine mixed in a 2:1 molar ratio. A rocking cell test was performed on each of the four AA-LDHIs.

The AA-LDHIs were tested in a bank of high pressure rocking cells. Each cell is outfitted with clear sapphire tubes housed and sealed in a Hastelloy body. The sapphire tubes allow for visual observation of the pressurized, cooled fluids inside the cell. The cells were isolated from each other and were equipped with pressure transducers and proximity sensors. A magnetic ball provided agitation as the cells are rocked back and forth at a predetermined angle and rate. The cells were submerged in a temperature controlled bath consisting of glycol and water.

The temperature and rocking was pre-programmed and automated. Each cell was pressurized independently and the pressure in monitored and recorded, along with the temperature data and signals from the proximity sensors.

The Four AA-LDHIs were tested under conditions which simulate a typical offshore pipeline in the Gulf of Mexico (GOM). Steady-state, shut-in and re-start processes were replicated. Test fluids (hydrocarbons and gas) were representative GOM are shown in Table 1.

TABLE 1

| Test Fluids | |
|---|---|
| Hydrocarbon: | Light GOM condensate |
| Aqueous: | 3.5% NaCl brine |
| Gas: | Structure II hydrate forming composition |

The gas composition was similar to GOM Green Canyon, a structure II hydrate former:

TABLE 2

| Type II Gas Composition | |
|---|---|
| Component | mol-% |
| Nitrogen | 0.39% |
| Methane | 87.26% |
| Ethane | 7.57% |
| Propane | 3.10% |
| iso-Butane | 0.49% |
| n-Butane | 0.79% |
| iso-Pentane | 0.20% |
| n-Pentane | 0.20% |

Tests were all conducted at constant volume. Inhibitor concentration varied from 1-5 vol-% based upon the total amount of water. The cells were initially pressurized at 20° C. to 2200 psig. Rocking was initialized at 15 rocks/min and an angle of ±25° off horizontal. At constant temperature of 20° C. the cells were rocked for 2 hours to mix the fluids and allow for the gas to saturate the fluids. The temperature was then ramped down continuously to 4° C. over a period of 2 hours while rocking.

After reaching 4° C., the cells were rocked for 12 hours at which time they were "shut-in". This phase consists of stopping the rocking with the cells in a horizontal position, simulating a pipeline shut-in. At the end of the shut-in period, rocking was re-started and the cells rocked for 2 hours. This was followed by a temperature ramp from 4° C. to 20° C. over a 2 hour period. Finally the cells were rocked at 20° C. for 2 hours. The final pressure was observed in order to insure the cells did not leak.

The performance of the chemicals was graded according to the following scale:

1. Stuck ball, low liquid level, large agglomerations or solid crystals, visible deposits on tube
2. Ball is free but resists rolling, moderate to little change in liquid level, large solid crystals, agglomerations that break up with agitation, no visible deposits on tube
3. Ball is free, no change in liquid level, viscous liquid, small dispersible agglomerations or crystals, no visible deposits on tube.
4. Ball is free, no change in liquid level, low viscosity, fine easily dispersed crystals, no large crystals
5. Ball is free, no change in liquid level, little to no change in viscosity, no visible deposits on tube or cylinder, extremely fine easily dispersible crystals.

Figure 4:
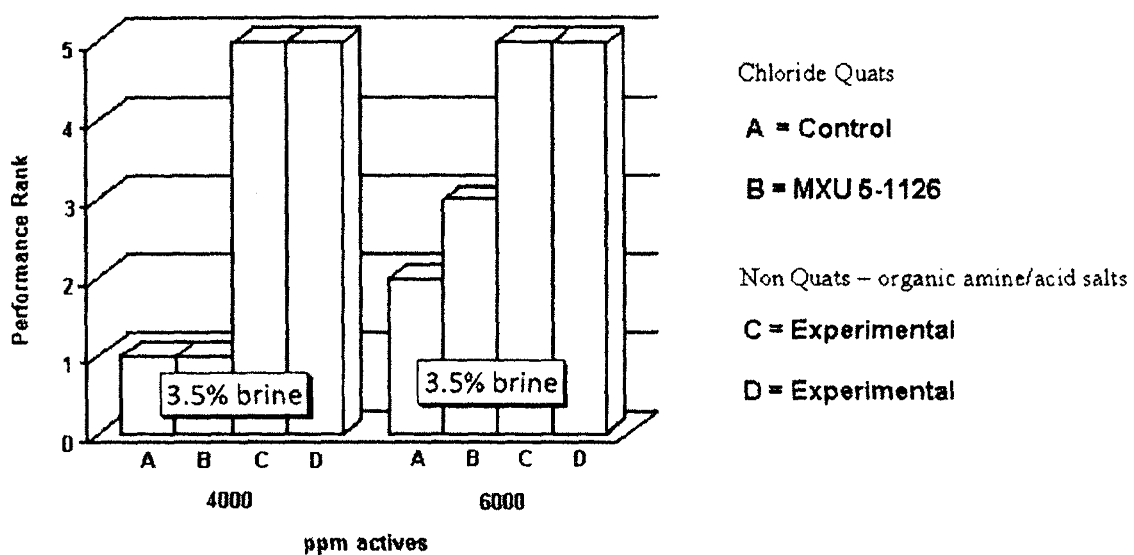
FIG. 4 shows the results of a comparison of the effectiveness of four anti-agglomerate compositions based on rating criteria.

FIG. 4 shows the results of the performance ranking.

| Hydrate Inhibitor | Rank |
|---|---|
| 1:1 benzoic acid/dimethyl palmitoyl amine | 5 |
| 1:1 maleic anhydride/dimethyl palmitoyl amine | 1 |
| 2:1 methanesulfonic acid/cocodiamine | 2 |
| 2:1 phthalic anhydride/cocodiamine | 5 |
| 2:1 salicylic acid/cocodiamine | 4 |

Although the invention has been described with reference to specific embodiments, this description is not meant to be constructed in a limited sense. Various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention, or their equivalents.

References Cited

The following publication is hereby incorporated by reference.

Kelland, Malcom A. "History of the Development of Low Dosage Hydrate Inhibitors." *Energy & Fuels, An American Chemical Society Journal*, vol. 20, May/June 2006.

What is claimed is:

1. A method of applying an anti-agglomerate hydrate inhibitor composition to a hydrocarbon stream comprising:

mixing an organic amine and an acid selected from the group consisting of a non-halide-containing inorganic acid, an organic acid, and mixtures thereof, to form a reaction product, wherein the reaction product is substantially free of halides containing compounds; and applying the reaction product to a hydrocarbon stream, wherein the anti-agglomerate hydrate inhibitor composition is applied to the hydrocarbon stream at an amount sufficient to form a concentration of about 0.05% to about 10% by weight of anti-agglomerate hydrate inhibitor in the hydrocarbon stream.

2. The method of claim 1 wherein the organic amine and acid are mixed in about a stoichiometric ratio.

3. The method of claim 1 wherein the anti-agglomerate hydrate inhibitor composition is applied continuously or in batch applications to the hydrocarbon stream.

4. The method of claim 1 wherein the anti-agglomerate hydrate inhibitor composition is applied to the hydrocarbon stream at an amount sufficient to form a concentration of about 0.2% to about 1.5% by weight of anti-agglomerate hydrate inhibitor in the hydrocarbon stream.

* * * * *